(12) United States Patent
Nasker (10) Patent No.: US 11,517,660 B2
(45) Date of Patent: Dec. 6, 2022

(54) SYRINGE ORGANIZER

(71) Applicant: Blanca Nasker, Boise, ID (US)

(72) Inventor: Blanca Nasker, Boise, ID (US)

( * ) Notice: Subject to any disclaimer, the term of this patent is extended or adjusted under 35 U.S.C. 154(b) by 0 days.

(21) Appl. No.: 16/052,498

(22) Filed: Aug. 1, 2018

(65) Prior Publication Data

US 2019/0038829 A1 Feb. 7, 2019

Related U.S. Application Data

(60) Provisional application No. 62/539,852, filed on Aug. 1, 2017.

(51) Int. Cl.
| | |
|---|---|
| *A61M 5/00* | (2006.01) |
| *A61B 50/22* | (2016.01) |
| *A47B 81/00* | (2006.01) |
| *A47F 5/00* | (2006.01) |
| *A47F 7/00* | (2006.01) |

(52) U.S. Cl.
CPC ............ *A61M 5/008* (2013.01); *A61B 50/22* (2016.02); *A47B 81/005* (2013.01); *A47F 5/00* (2013.01); *A47F 7/0021* (2013.01); *A47F 7/0028* (2013.01)

(58) Field of Classification Search
CPC .......... A61M 5/008; A61B 50/22; B01L 9/00; A47B 81/005; A47F 5/00; A47F 7/0021; A47F 7/0028
USPC ............ 211/60.1, 62, 65, 66, 69, 69.1, 69.5; 206/366, 443
See application file for complete search history.

(56) References Cited

U.S. PATENT DOCUMENTS

| | | | | |
|---|---|---|---|---|
| 431,862 A | * | 7/1890 | Abrams | A47F 5/112 |
| | | | | 211/69.9 |
| 565,710 A | * | 8/1896 | Tollner | A45C 11/34 |
| | | | | 206/214 |
| 1,163,672 A | * | 12/1915 | Kulow | B43L 25/10 |
| | | | | 211/69.4 |
| 1,647,039 A | * | 10/1927 | Fischer | G01N 9/14 |
| | | | | 248/309.1 |

(Continued)

FOREIGN PATENT DOCUMENTS

JP 10005332 A * 1/1998

*Primary Examiner* — Devin K Barnett
(74) *Attorney, Agent, or Firm* — Scott D. Swanson; Shaver & Swanson, LLP (57) ABSTRACT

What is disclosed is an organizational rack for organizing and storing syringes. The organizational rack is particularly useful in storing syringes that are utilized for dispensing an oral medication. This rack includes a base from which a series of projections emanate. This includes a base projection into which a cap of a syringe for oral dispensing of medicine is placed. The device utilizes a second projection that incorporates openings or notches into which the barrel of the syringe fits. The rack has a third projection that utilizes an opening. The space between the third projection and the first projection is configured such that when a syringe cap is placed in an opening in the first projection, the barrel of the syringe fits between the first projection and the third projection such that friction is placed on the finger grips of the syringe to hold the syringe in place. The base has a fourth projection or flange at a second end of the base that serves to protect an extended syringe from accidental or intentional depression unless the syringe is removed from the organizational rack.

14 Claims, 8 Drawing Sheets

(56) References Cited

U.S. PATENT DOCUMENTS

| | | | | | |
|---|---|---|---|---|---|
| 1,705,656 | A * | 3/1929 | Blackman | B43M 99/003 | 211/69.6 |
| 1,728,642 | A * | 9/1929 | Travor | B43M 99/003 | 211/69.7 |
| 1,841,753 | A * | 1/1932 | Merkle | A47F 5/112 | 211/65 |
| 1,897,672 | A * | 2/1933 | Neumann | B65D 5/504 | 206/315.2 |
| 1,975,512 | A * | 10/1934 | Huott | B43L 27/02 | 15/257.073 |
| 2,110,007 | A * | 3/1938 | Tefft | B43M 99/003 | 211/69.7 |
| 2,113,633 | A * | 4/1938 | Stempel | B43M 99/003 | 211/69.7 |
| 2,151,440 | A * | 3/1939 | Pollak | B43M 99/003 | 211/69.7 |
| 2,175,657 | A * | 10/1939 | Ashley | B43L 25/10 | 15/257.05 |
| 2,313,905 | A * | 3/1943 | Wallin | A61M 5/008 | 211/60.1 |
| 2,460,230 | A * | 1/1949 | Makrianes | B65D 5/504 | 211/70.1 |
| 2,472,028 | A * | 5/1949 | Son | A61L 2/26 | 206/365 |
| D167,891 | S * | 10/1952 | Hallward | D6/534 | |
| 2,629,499 | A * | 2/1953 | Welshenbach | B65D 5/504 | 206/315.2 |
| 2,645,353 | A * | 7/1953 | Anderson, Jr. | A63B 55/10 | 206/315.2 |
| 2,659,485 | A * | 11/1953 | Duley | A61M 5/008 | 131/240.1 |
| 2,846,806 | A * | 8/1958 | Gaines | A01K 97/06 | 206/315.1 |
| D185,600 | S * | 6/1959 | Gaither | D21/519 | |
| 2,929,510 | A * | 3/1960 | Penn | A61M 5/32 | 211/60.1 |
| D194,087 | S * | 11/1962 | Jenkins | D24/229 | |
| 3,063,449 | A * | 11/1962 | Schultz | A61M 3/00 | 604/181 |
| 3,076,455 | A * | 2/1963 | McConnaughey | A61M 5/24 | 604/232 |
| 3,084,790 | A * | 4/1963 | Lugt, Jr. | B65D 5/4802 | 206/562 |
| 3,133,635 | A * | 5/1964 | Morris | A61M 5/002 | 206/366 |
| D200,815 | S * | 4/1965 | Chard | D24/229 | |
| 3,532,222 | A * | 10/1970 | Madden | B44D 3/04 | 211/65 |
| 3,727,749 | A * | 4/1973 | Martin | A45C 11/34 | 206/366 |
| 3,802,844 | A * | 4/1974 | Sendra | B01L 9/06 | 211/74 |
| D248,871 | S * | 8/1978 | Forsman | D24/230 | |
| D291,268 | S * | 8/1987 | Stephenson | A46B 17/04 | D6/534 |
| D293,469 | S * | 12/1987 | Greenblatt | D24/229 | |
| 4,753,345 | A * | 6/1988 | Goodsir | A61M 5/008 | 206/365 |
| 4,929,427 | A * | 5/1990 | Guala | G01N 15/05 | 206/366 |
| 4,971,200 | A * | 11/1990 | Huang | B65D 21/0235 | 206/420 |
| 4,974,728 | A * | 12/1990 | Colton | A61M 5/3213 | 206/366 |
| 5,084,028 | A * | 1/1992 | Kennedy | A61M 5/3213 | 128/919 |
| 5,099,992 | A * | 3/1992 | Heimreid | A61J 1/2096 | 206/366 |
| 5,123,534 | A * | 6/1992 | Chwang | B65D 85/42 | 206/419 |
| 5,133,454 | A * | 7/1992 | Hammer | A61M 5/002 | 206/364 |
| 5,168,999 | A * | 12/1992 | Lee | B65D 25/105 | 206/420 |
| D334,973 | S * | 4/1993 | Valentine | D24/227 | |
| D337,830 | S * | 7/1993 | Coyne | D24/227 | |
| 5,267,652 | A * | 12/1993 | Carroll | B26D 7/01 | 206/585 |
| 5,279,578 | A * | 1/1994 | Cooke | A61M 5/3213 | 206/365 |
| 5,299,687 | A * | 4/1994 | Hanifl | B01L 9/543 | 206/364 |
| 5,317,491 | A * | 5/1994 | Lee | A47F 7/005 | 206/420 |
| 5,339,955 | A * | 8/1994 | Horan | A61B 50/33 | 206/350 |
| 5,356,385 | A * | 10/1994 | Latini | A61M 5/3213 | 206/366 |
| D354,988 | S * | 1/1995 | Garza | D12/420 | |
| 5,494,166 | A * | 2/1996 | Kuwata | B65D 5/5011 | 206/443 |
| 5,498,242 | A * | 3/1996 | Cooke | A61M 5/3213 | 128/919 |
| D370,338 | S * | 6/1996 | Quist | D3/205 | |
| 5,597,070 | A * | 1/1997 | Wu | B65D 5/504 | 206/419 |
| 5,641,078 | A * | 6/1997 | Kaufmann | B43L 25/008 | 15/257.075 |
| 5,678,700 | A * | 10/1997 | Crosson, Jr. | A01K 97/10 | 211/60.1 |
| 5,732,821 | A * | 3/1998 | Stone | A61L 2/26 | 206/365 |
| 5,762,202 | A * | 6/1998 | Atad | A61C 19/02 | 206/369 |
| 5,938,040 | A * | 8/1999 | Goodwin | B43M 99/006 | 206/214 |
| 6,101,760 | A * | 8/2000 | Garman | A01K 97/06 | 43/57.1 |
| 6,244,447 | B1 * | 6/2001 | Frieze | A61L 2/07 | 206/370 |
| 6,257,408 | B1 * | 7/2001 | Odierno | A61M 5/008 | 206/365 |
| 6,387,330 | B1 * | 5/2002 | Bova | B01J 19/0046 | 141/102 |
| 6,484,892 | B1 * | 11/2002 | Gooner | B25H 3/04 | 211/70.6 |
| 6,783,004 | B1 * | 8/2004 | Rinner | A61B 17/8875 | 206/368 |
| 6,955,259 | B1 * | 10/2005 | Jesse | A61M 5/008 | 206/366 |
| 7,299,935 | B2 * | 11/2007 | Skaley | F16L 3/223 | 211/60.1 |
| D613,418 | S * | 4/2010 | Ryan | D24/229 | |
| 7,806,262 | B2 * | 10/2010 | Sakai | B65D 5/504 | 206/366 |
| 8,752,700 | B1 * | 6/2014 | Hoftman | A61B 17/3217 | 206/355 |
| 8,955,697 | B2 * | 2/2015 | Spilotro | A47B 81/00 | 211/60.1 |
| D726,330 | S * | 4/2015 | Hurst | D24/227 | |
| 9,907,727 | B2 * | 3/2018 | Sharpe | A61J 1/16 | |
| 2001/0035362 | A1 * | 11/2001 | Odierno | A61M 5/008 | 206/366 |
| 2003/0024891 | A1 * | 2/2003 | Diamond | A61M 5/008 | 211/85.13 |
| 2003/0034315 | A1 * | 2/2003 | Tayebi | A47K 1/09 | 211/65 |
| 2004/0074795 | A1 * | 4/2004 | Fischer | A61C 19/02 | 206/366 |
| 2005/0101905 | A1 * | 5/2005 | Merry | A61M 5/008 | 604/19 |
| 2005/0194331 | A1 * | 9/2005 | Chang | A47B 81/00 | 211/60.1 |
| 2005/0249651 | A1 * | 11/2005 | Riley | A61L 2/26 | 422/300 |
| 2005/0265901 | A1 * | 12/2005 | Sinclair | B01L 9/06 | 422/552 |

(56) References Cited

U.S. PATENT DOCUMENTS

| | | | |
|---|---|---|---|
| 2006/0032828 A1* | 2/2006 | Chiu | A47B 13/02 211/66 |
| 2007/0009408 A1* | 1/2007 | Riley | A61L 2/26 422/300 |
| 2008/0251475 A1* | 10/2008 | Lambert | A47K 1/09 211/65 |
| 2009/0127214 A1* | 5/2009 | Kruger | A47B 88/90 211/65 |
| 2010/0012537 A1* | 1/2010 | Farrar | A61M 5/002 206/364 |
| 2010/0051491 A1* | 3/2010 | Lampropoulos | A61M 5/008 206/366 |
| 2012/0175328 A1* | 7/2012 | Bosch | B01L 9/06 211/85.18 |
| 2015/0238686 A1* | 8/2015 | Mohyi | A61M 5/008 206/364 |
| 2015/0239278 A1* | 8/2015 | White | B43K 23/001 211/69.5 |
| 2016/0136352 A1* | 5/2016 | Smith | B65D 25/103 206/366 |
| 2018/0121630 A1* | 5/2018 | Portnoy | G06F 19/3468 |
| 2018/0318494 A1* | 11/2018 | Grindinger | A61M 5/002 |

* cited by examiner

SYRINGE ORGANIZER

PRIORITY/CROSS-REFERENCE TO RELATED APPLICATIONS

This application claims the benefit of U.S. Provisional Application No. 62/539,852, filed Aug. 1, 2017, the disclosure of which is incorporated by reference.

TECHNICAL FIELD

The disclosure generally relates to the field of healthcare. Particular embodiments relate to transportation and organization of syringes.

SUMMARY OF THE DISCLOSURE

The invention is an organizer rack for securing and presenting loaded oral administration syringes so they can be very visible for purposes of inventory and verification. The invention could conceivably be used for other types of syringes as well. Each oral administration syringe has a tip dispenser, a cap, a plunger, a medication tube, and finger grip bars at the top of the medication tube. The rack is generally planar, and made of any material that serves the purposes of the device, such as paper, plastic, metal, or composite materials. The rack has features on the front side of the rack for securing the syringes. These include a row of cap receptacles, the cap receptacles shaped to receive the caps which are placed on syringes. Above the cap receptacles is a row of paired grip fingers, which protrude and which enclose a space in which the medication tube of the syringe fits. It secures the syringe so they don't fall off the rack, but they can be removed easily when desired. Above the grip fingers is a slot in which the finger grip of the syringes fit, and further secure they syringes. What is disclosed is a syringe organizer rack for securing a plurality of syringes. A typical syringe has a tip dispenser, a cap over the tip dispenser, a plunger comprising a shaft, a medication tube, and finger grip bars at the top of the medication tube.

The organizer rack has a base. The base has a generally planar section having front side and a back side and comprising a width and a length. The base has first projection extending from the front side of the base. The first projection has a plurality of cap receptacles aligned in a row on the first projection. The cap receptacles are configured to receive and secure a syringe cap when the syringe cap is attached to a syringe. In a preferred embodiment the first projection defines a first edge of the base. The cap receptacles can be a variety of shapes including a square opening and a round opening. In a preferred embodiment the openings in the first projection do not form a tunnel through the first projection and instead only penetrate partially through the first projection.

In a preferred embodiment, the base has a second projection extending from the front side of the base. The said second projection is oriented generally parallel to the first projection. The second projection has a plurality of openings configured to receive a medication tube, also called the barrel of the syringe. The openings are generally aligned with the cap receptacles in the first projection. The openings are configured to retain a medication tube of a syringe when the medication tube is inserted in the opening. In a preferred embodiment the opening is a semi-circular opening. In a further preferred embodiment the opening is generally a ¾ circular opening such that force is required to place the syringe barrel into the opening and to remove it (the opening is narrower at its neck than at a center). In an embodiment the second projection comprises releasable attachment.

In a preferred embodiment, the base has a third projection extending from the front side of the base. The third projection is oriented generally parallel to the first projection. The third projection has a plurality of openings configured for passage of shaft of a plunger. The third projection is positioned to be proximate to a finger grip of a syringe retained in said rack. In a preferred embodiment the third projection has a first side and a second side. In an embodiment the first side is configured to impart friction on a finger grip of each syringe to retain the syringe in the rack.

In a preferred embodiment the base has a fourth projection. The fourth projection is configured to prevent an object, such as a user's hand or any other object that could be bumped against the syringe, from depressing an extended plunger on a syringe when the syringe is retained in the rack. In a preferred embodiment the fourth projection defines a second edge of the base opposite from the first edge discussed above.

In a preferred embodiment the rack is configured to retain ten syringes. In a preferred embodiment the rack is configured to retain syringes oriented in a direction parallel to the width of the rack. In this orientation the first projection, second projection, third projection, and fourth projection are oriented along the width of said rack. The rack can be constructed with a generally parallel lengthwise projections configured to define separate channels configured to distinguish areas for separate syringes.

In a preferred embodiment, the first projections of the syringe rack are generally square in shape and the openings in the first projection do not extend through the first projection.

DETAILED DESCRIPTION OF THE PREFERRED EMBODIMENTS

While the presently disclosed inventive concept(s) is susceptible of various modifications and alternative constructions, certain illustrated embodiments thereof have been shown in the drawings and will be described below in detail. It should be understood, however, that there is no intention to limit the inventive concept(s) to the specific form disclosed, but, on the contrary, the presently disclosed and claimed inventive concept(s) is to cover all modifications, alternative constructions, and equivalents falling within the spirit and scope of the inventive concept(s) as defined herein.

In the following description and in the figures, like elements are identified with like reference numerals. The use of "e.g.," "etc," and "or" indicates non-exclusive alternatives without limitation unless otherwise noted. The use of "including" means "including, but not limited to," unless otherwise noted.

Figure 1A:
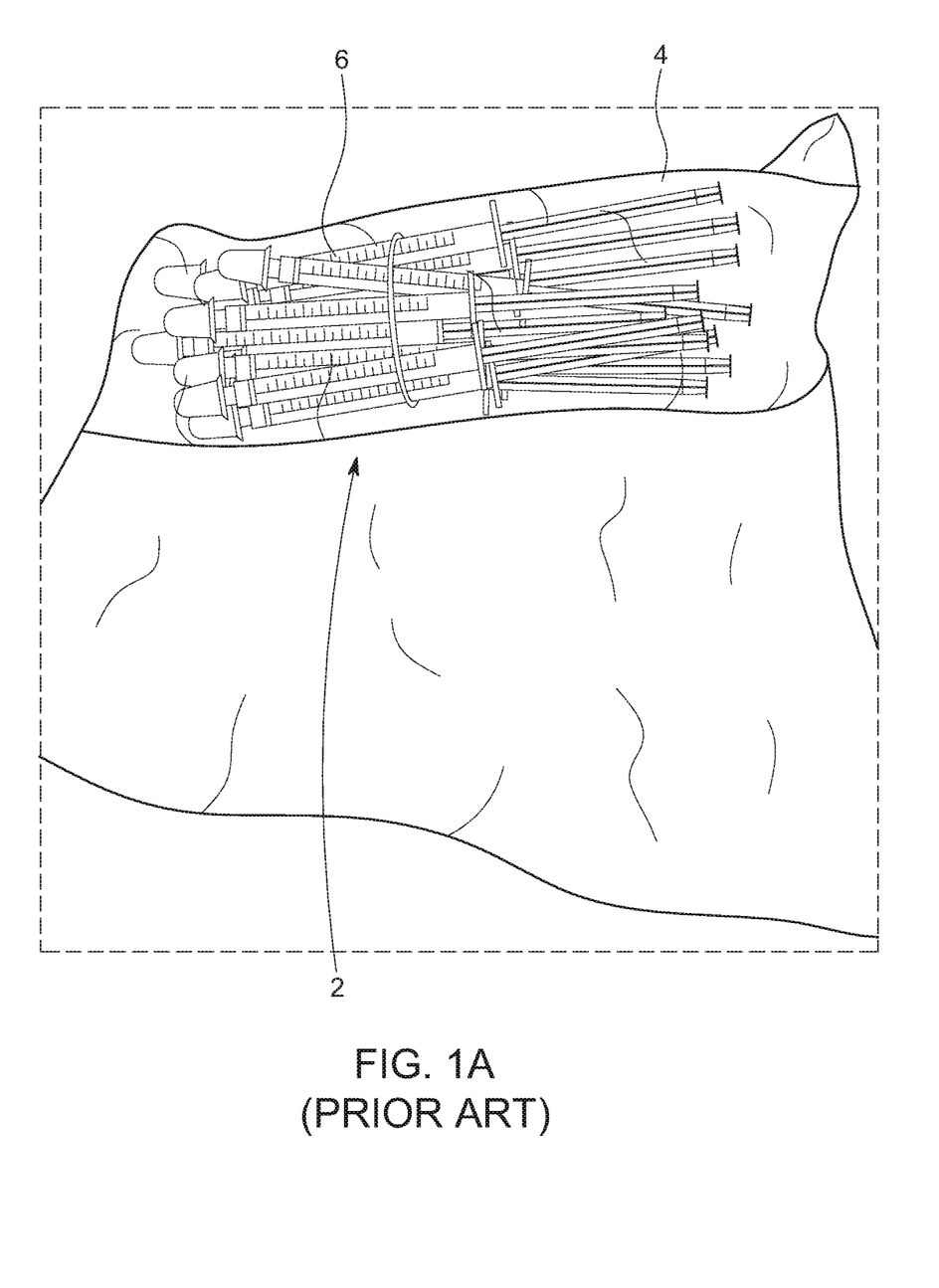
FIG. 1A illustrates a prior art version of a mechanism for carrying and distributing syringes of oral medication.

FIG. 1A illustrates a typical mechanism by which a series of syringes for a specific client in a hospital are prepared and transported for administration by a nurse or other healthcare worker. The typical syringe provider involves utilizing a series of syringes in a bag 2. The syringes 6 are typically prepared with appropriate doses for a patient and placed into a bag 4. This can involve, for example, the medication doses for the patient for the entire day or for multiple days. An issue arises when the bag of syringes is provided to a nurse for administering the drugs. It is often difficult for the nurses or other hospital staff to keep track of which syringes have been administered and which syringes need to be administered in the future and when. Unfortunately this can lead to overdosing of patients or patients missing their medications. What is needed is a system and method of providing a plurality of syringes such that hospital staff can easily determine which syringe to administer and when.

Figure 1B:
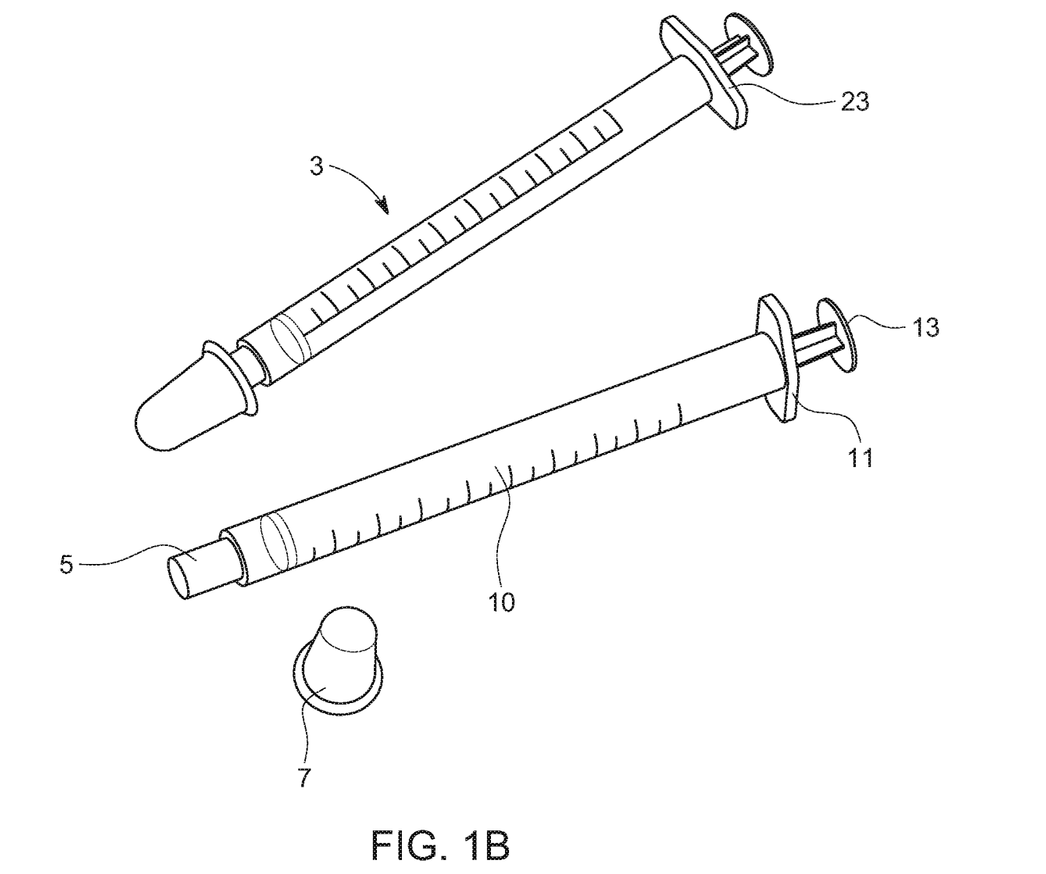
FIG. 1B illustrates an embodiment of a typical syringe utilized for oral dispensing of medication.

FIG. 1B illustrates an oral administration syringe 3 with a tip dispenser 5, a cap 7, a medication tube/barrel 10, finger grip at the top of the medication tube 11, and a plunger 13.

Figure 2:
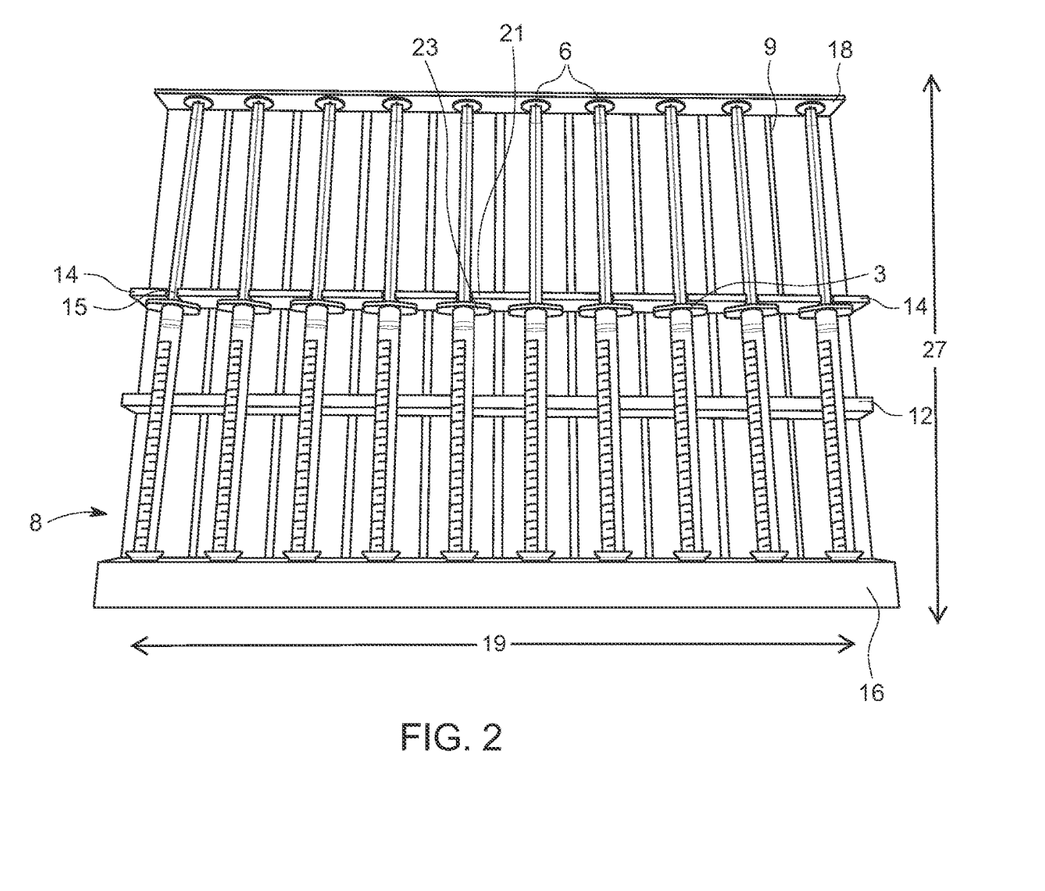
FIG. 2 illustrates a front perspective view of an organizational rack for storing syringes for oral dispensing of medication.

FIG. 2 illustrates a front view of a first embodiment of the invention. Provided is an organizational rack 8 for organizing syringes according to their content and/or administration dates or times. The rack utilizes a base 9, in the depicted embodiment for example a flat section of material from which extend retaining mechanisms for holding a syringe in place. The base has a bottom retainer section 16 that retains the barrel of the syringe in a depression or opening (depicted without a syringe in FIG. 8). Alternatively, the cap can be retained by the bottom retainer as shown in FIG. 1. A second retainer mechanism 12 is utilized to retain an upper portion of the barrel of the syringe. In the depicted embodiment the second retainer mechanism is a projection extending from the base and spanning the width of the base. The extension utilizes openings in the projection that are slightly larger than the barrel of the syringe to retain the syringe utilizing friction between the projection and the barrel of the syringe. Preferably, the syringe 6 is retained in the organizational rack 8 in a manner generally parallel to the width 27 and generally perpendicular to the length 19.

When extended, the barrel of the syringe extends to just shy of an upper projection 18 which prevents unintentional depression of the plunger thus expelling the material within the syringe. The syringe is retained in FIG. 2 by the finger grip retention mechanism 14. The finger grip retention mechanism in a preferred embodiment is a projection from the base which has openings having a width larger than the syringe but smaller than the width of the syringe at the finger projections of the syringe. In the depicted preferred embodiment the finger grip retention mechanism is positioned such that the barrel of the syringe is located such that when the tip of the syringe is positioned within an opening in the bottom retainer section 16, the barrel of the finger grips of the syringe are placed within the rack such that there is friction between a first side of the finger grip retention mechanism 21 and a first side 23 of the finger grip of the syringe. This retention mechanism can be a notch into which the plunger arm is placed, double sided sticky tape, or a variety of other mechanisms. The rack can include indicia indicating the date, number, or time of which each syringe is to be administered.

Figure 3:
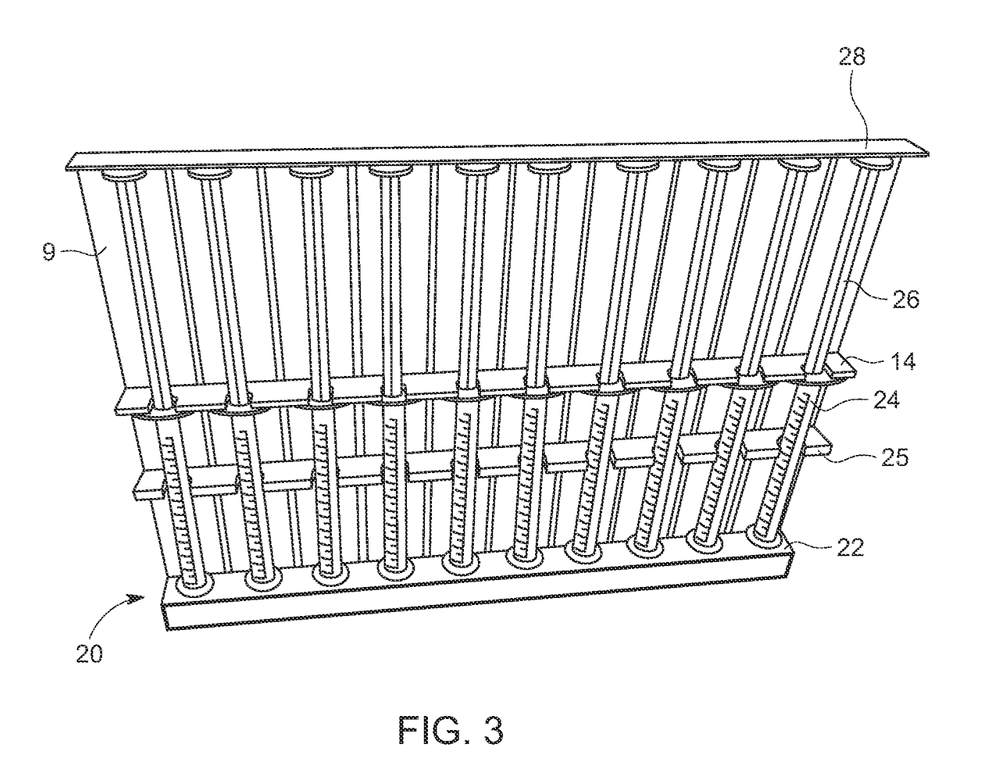
FIG. 3 illustrates a perspective view of an organizational rack for storing syringes for oral dispensing of medication.

FIG. 3 illustrates a plurality of syringes attached to the rack 20. As shown, the plunger 26 of each syringe extends to the fourth projection in an extended position. The fourth projection serves to protect the extended plunger from being depressed 28. The barrel 24 of the syringe is retained by the second projection 25 and the first projection 22 retains the lower portion of the barrel or the protective cap that protects the tip dispenser of the syringe. Alternatively a needle protector can be used if syringes incorporating needles are used.

In FIG. 3 the first projection 22 forms a lower or first edge of the base 9 within a lower edge of the unit. The second projection is a projection having notches or cutouts 25 attached to or integral with the base 9 into which the barrel of the syringe fits. For example, each projection can be made out of foam or other soft material such that the barrel of the syringe can be placed in and pushed into the notches or in the alternative a rigid material that forms an opening, or out of a rigid material. This includes manufacture via injection molding, 3D printing, and any other manufacturing method known to those of skill in the art. The third projection 14 includes a notch or opening through which the barrel of the plunger can be placed. In a preferred embodiment a side of the third projection provides friction to the finger grips of the syringe to retain the syringe in the rack.

Figure 4:
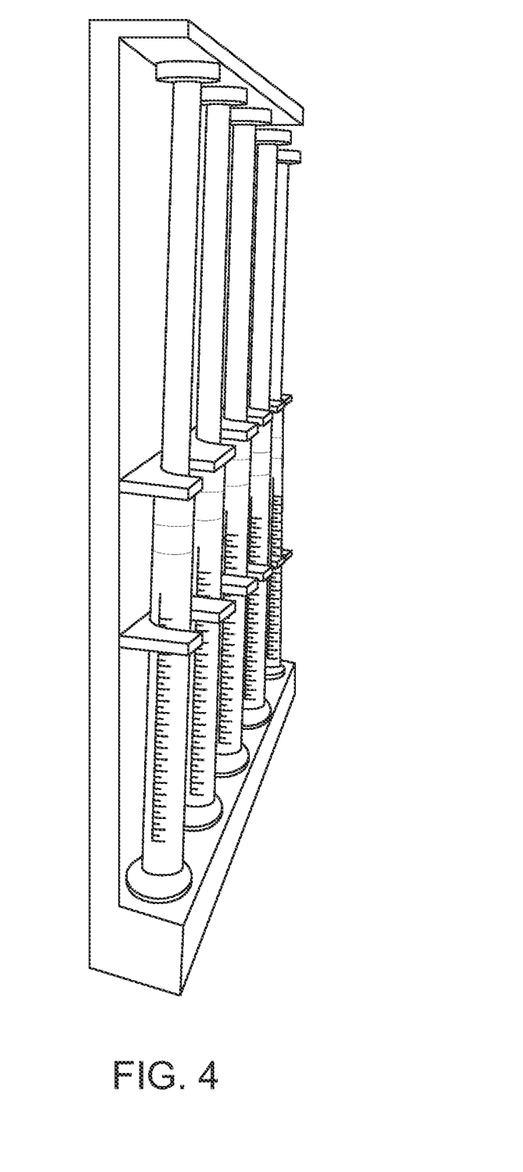
FIG. 4 illustrates a first side perspective view of an organizational rack for storing syringes for oral dispensing of medication.

FIG. 4 illustrates a first side view of an organizational rack for storing syringes for oral dispensing of medication.

Figure 5:
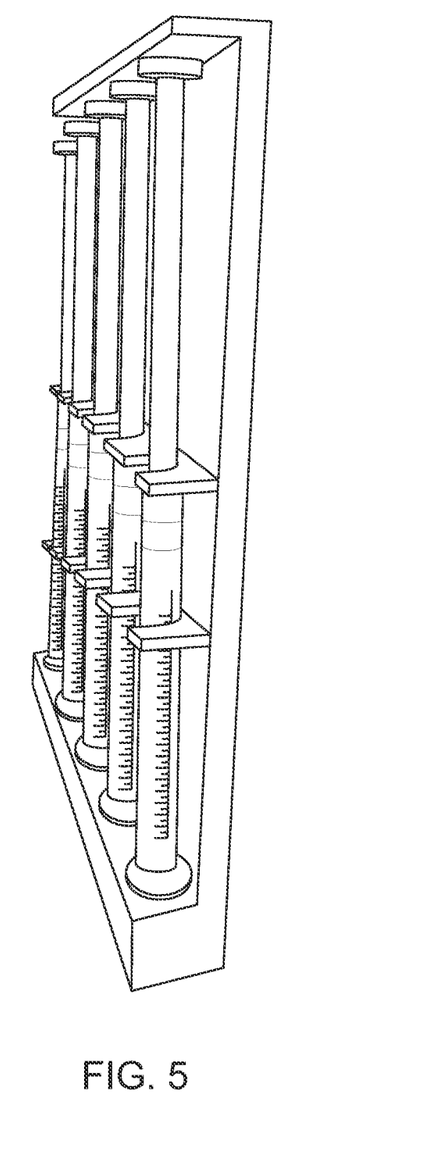
FIG. 5 illustrates a second side view of a rack for holding syringes for dispensing an oral medication.

FIG. 5 illustrates a second side view of a rack for holding syringes for dispensing an oral medication.

Figure 6:
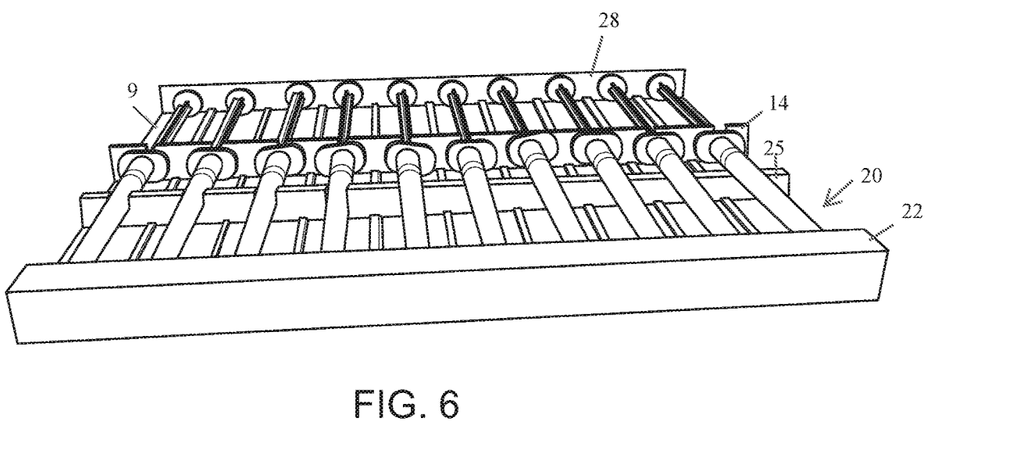
FIG. 6 illustrates a bottom perspective view of an organizational rack for holding syringes for dispensing an oral medication.

FIG. 6 illustrates a bottom perspective view of an organizational rack for holding syringes for dispensing oral medication.

Figure 7:
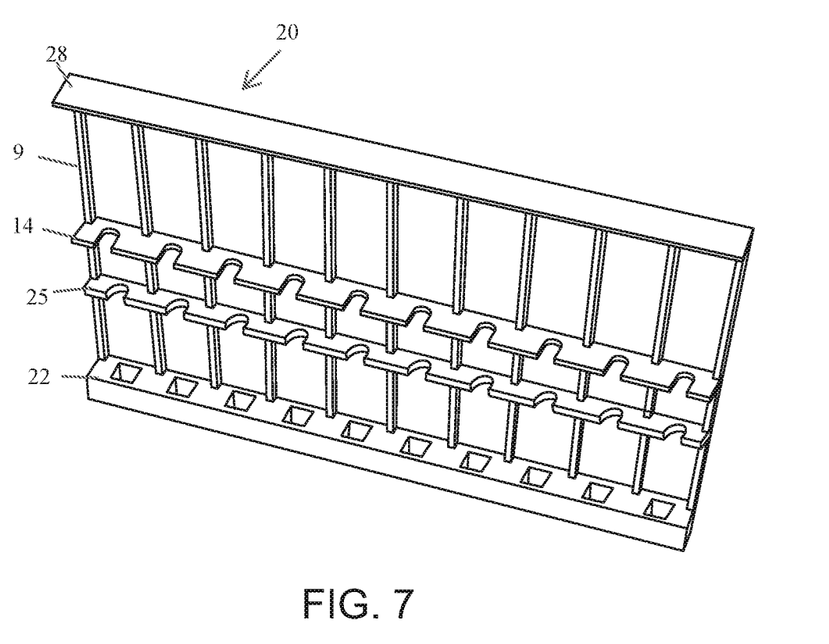
FIG. 7 illustrates a perspective view of an organizational rack for syringes for dispensing an oral medication.
Figure 8:
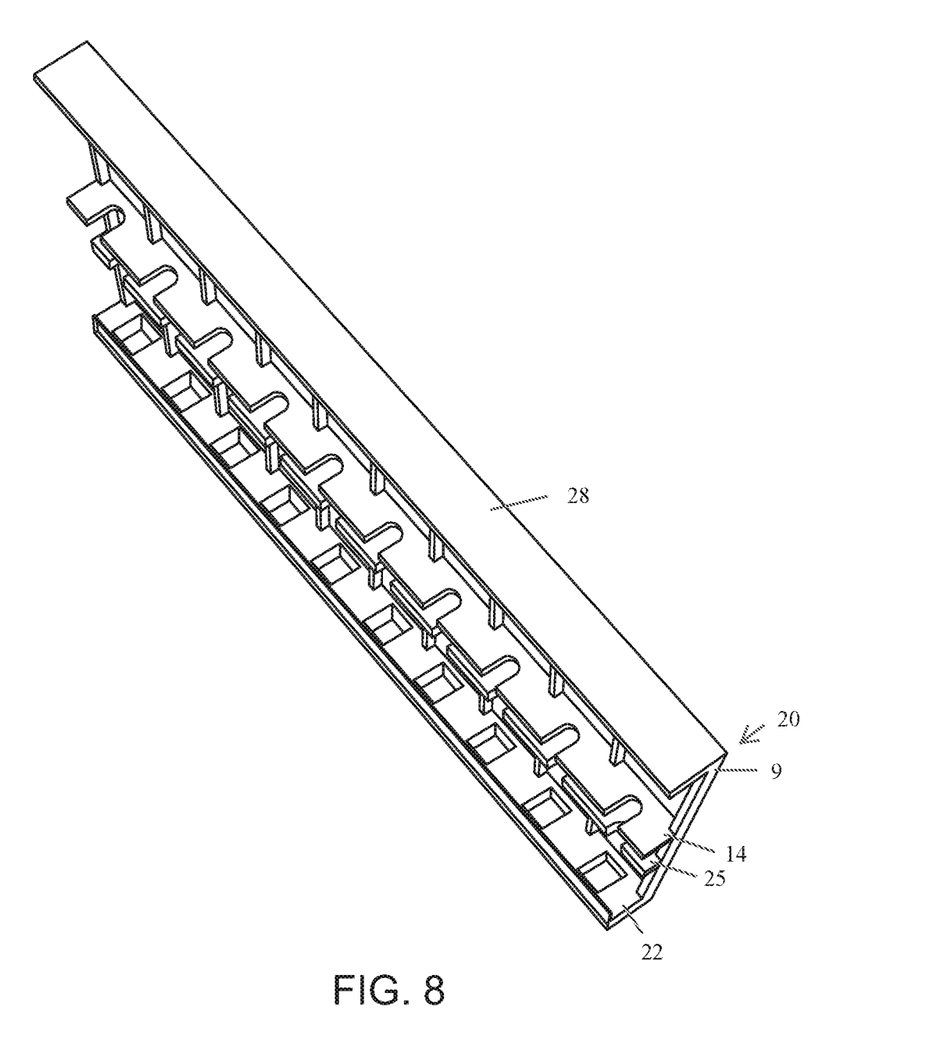
FIG. 8 illustrates a top perspective view of the embodiment shown in FIG. 7.

FIGS. 7 and 8 illustrate views of a preferred embodiment of the invention without syringes being retained in the invention. The openings in the first projection and through the second and third projections are depicted. The second projection is shown with an approximately ¾ circular opening having a neck larger than a center of the opening.

The base of the rack can have indicia indicating the patient's name, the date of the order of the syringes, and a variety of other useful indicia on the back of the rack (not shown).

Still other features and advantages of the presently disclosed and claimed inventive concept(s) will become readily apparent to those skilled in this art from the following detailed description describing preferred embodiments of the inventive concept(s), simply by way of illustration of the best mode contemplated by carrying out the inventive concept(s). As will be realized, the inventive concept(s) is capable of modification in various obvious respects all without departing from the inventive concept(s). Accordingly, the drawings and description of the preferred embodiments are to be regarded as illustrative in nature, and not as restrictive in nature.

While certain exemplary embodiments are shown in the Figures and described in this disclosure, it is to be distinctly understood that the presently disclosed inventive concept(s) is not limited thereto but may be variously embodied to practice within the scope of this disclosure. From the foregoing description, it will be apparent that various changes may be made without departing from the spirit and scope of the disclosure as defined herein.

What is claimed is:

1. A syringe organizer rack in combination with a plurality of needleless syringes comprising:

a base comprising a planar section having front side and a back side, said base further comprises a width and a length;

a series of spaced apart generally parallel projections, wherein each projection from said series of spaced apart generally parallel projections extends longitudinally along said length of said base; wherein said series of spaced apart generally parallel projections comprises a first projection, a second projection, a third projection, and a fourth projection;

each of said needleless syringes comprises: a medication tube having a needleless tip dispenser, a hollow shaft extending from said needleless tip dispenser to a finger grip defining an opening configured for sliding engagement therethrough of a plunger, wherein said finger grip comprises a planar finger flange extending beyond a circumference of said hollow shaft, said plunger having a first end and a second end, said second end of said plunger configured with a planar thumb tab configured for depression by a user's thumb when a user grasps the syringe with two fingers positioned on said planar finger flange on opposing sides of said medication tube, wherein said plunger is positioned in said hollow shaft such that said plunger is configured to move in said hollow shaft from an extended position wherein said plunger is extended such that said first end of said plunger is proximate to said finger grip to a dispensed position wherein said second end of said plunger is positioned proximate to said finger grip and said first end of said plunger is positioned proximate to said tip dispenser, wherein said syringe is configured to update a medication in said syringe when said plunger moves from said dispensed position to said extended position, wherein each needleless syringe is configured to dispense medication when each planar thumb tab is depressed causing each needleless syringe to move from said extended position to said dispensed position respectively;

wherein said first projection comprising a plurality of cap receptacles aligned in a row in said first projection, said cap receptacles configured to receive and secure said caps attached to said needleless syringes, said plurality of cap receptacles each comprising an opening in one side of said first projection and configured for insertion of a cap from a direction parallel to said width, wherein said first projection encircles said openings of said plurality of cap receptacles such that each of said openings are configured for insertion of each cap from a direction parallel to said width;

wherein said second projection comprises a plurality of second projection openings, wherein each medication tube of said plurality of needleless syringes is positioned in one of said plurality of second projection openings, wherein said second projection openings are aligned with said cap receptacles in said first projection;

wherein said third projection comprises a plurality of third projection openings configured for passage of shaft of a plunger, wherein said third projection is positioned proximate to said finger grip of each of said needleless syringes;

wherein said fourth projection extends from said back adjacent to said planar thumb tab and is configured to prevent an object from depressing said planar thumb tab of each of said plungers of said needleless syringes when said plungers are in said extended position said medication tubes are retained in said third projection openings and said plunger of said needleless syringes passing through said third projection opening;

wherein said cap receptacles and said third projection are spaced apart such that said cap is positioned within said cap receptacle and a top side of said finger grip is positioned against a bottom side of said third projection so as to retain said medication tube of each of said needleless syringes between said first projection and said third projection, wherein said third projection and said fourth projection are spaced apart such that a top side of said planar thumb tab is positioned adjacent to a bottom side of said fourth projection when said plunger is in said extended position.

2. The syringe rack of claim 1, wherein said rack is configured to retain ten needleless syringes.

3. The syringe rack of claim 1, wherein said rack is configured to retain needleless syringes oriented in a direction parallel to said width of said rack, wherein said first projection, second projection, third projection, and fourth projection are oriented along said width of said rack, wherein said rack comprises a series of generally parallel lengthwise projections configured to define separate channels configured for separate needleless syringes.

4. The syringe rack of claim 1, wherein said first projection defines a first edge of said base.

5. The syringe rack of claim 1, wherein said fourth projection defines a second edge of said base.

6. The syringe rack of claim 4, wherein said fourth projection defines a second edge of said base.

7. The syringe rack of claim 1, wherein said second projection openings comprise generally semi-circular openings.

8. The syringe rack of claim 1, wherein said second notches define generally comprise ¾ of a circle openings.

9. The syringe rack of claim 1, wherein said first projection comprises a generally square cross-sectional shape, wherein said cap receptacles in said first projection do not extend through said first projection.

10. The syringe rack of claim 1, wherein said first projection comprises a length, wherein said length of said first projection is the same as the length of the base.

11. The syringe rack of claim 1, wherein said second projection comprises a length, wherein said length of said second projection is the same as the length of the base.

12. The syringe rack of claim 1, wherein said third projection comprises a length, wherein said length of said third projection is the same as the length of the base.

13. (The syringe rack of claim 1, wherein said fourth projection comprises a length, wherein said length of said fourth projection is the same as the length of the base.

14. The syringe rack of claim 1, wherein said fourth projection comprises a flat surface configured to prevent an object from depressing said plungers of said plurality of needleless syringes.

* * * * *